United States Patent [19]

Razumney

[11] 4,370,206

[45] Jan. 25, 1983

[54] METHOD OF OPERATING AN ELECTROCHEMICAL GAS MEASURING SYSTEM

[75] Inventor: Gerardo A. Razumney, Philadelphia, Pa.

[73] Assignee: Rexnord, Incorporated, Milwaukee, Wis.

[21] Appl. No.: 813,394

[22] Filed: Jul. 6, 1977

[51] Int. Cl.³ .................... G01N 27/28; G01N 27/54
[52] U.S. Cl. .................................................. 204/1 T
[58] Field of Search ............... 204/195 R, 195 P, 1 T, 204/1 F, 1 N, 1 K

[56] References Cited

U.S. PATENT DOCUMENTS

| | | | |
|---|---|---|---|
| 2,851,654 | 9/1958 | Haddad | 204/195 R |
| 3,622,488 | 11/1971 | Chand et al. | 204/195 P |
| 3,691,023 | 9/1972 | Ruka et al. | 204/195 S |
| 3,763,025 | 10/1973 | Chand | 204/195 R |
| 3,776,832 | 12/1973 | Oswin et al. | 204/195 R |
| 4,017,373 | 4/1977 | Shaw et al. | 204/195 R |
| 4,025,412 | 5/1977 | LaConti | 204/195 R |

OTHER PUBLICATIONS

LaConti et al, "J. of the Electrochemical Society-Electrochemical Technology", vol. 118, (1971), pp. 506-510.

Primary Examiner—G. L. Kaplan
Attorney, Agent, or Firm—Jim Zegeer

[57] ABSTRACT

There is disclosed an electrochemical gas detector system utilizing a polarized gas diffusion sensing electrode which is exposed to a gas mixture containing an electrochemically oxidizable or reducible gas, such as CO, $H_2$, $H_2S$, $SO_2$, NO, $NO_2$ and $CH_4$ which electrode has a suitable catalyst, such as platinum, iridium, ruthenium, gold, etc., as the active element at which the gas is electrochemically oxidized or reduced, a nonpolarizable, reversible counter electrode constituted by a suitable redox couple, preferably of the type metal/metal salt, such as Ag/AgCl or metal/metal oxide, such as Hg/HgO, or metal oxide/metal salt, such as $PbO_2/PbSO_4$, and a liquid electrolyte body in contact with both electrodes to constitute a complete electrochemical cell. A constant potential difference is applied between the electrodes which biases the sensing electrode to a selected portion of the electrochemical current-voltage curve for oxidation or reduction of the reducible gas. Means are provided for indicating current flowing between the electrodes as a measure of the concentration of the gas at the sensing electrode.

4 Claims, 6 Drawing Figures

METHOD OF OPERATING AN ELECTROCHEMICAL GAS MEASURING SYSTEM

BACKGROUND OF THE INVENTION

La Conti and Maget in the Journal of the Electrochemical Society: Electrochemical Technology 118-pages 506–510 (1971) disclose an electrochemical sensor for detecting $H_2$, CO and hydrocarbons in inert or oxygen-containing atmospheres. The sensor is constituted by a gas diffusion electrode, using platinum on boron carbide, a sulfuric acid electrolyte and counter electrode constituted by lead dioxide ($PbO_2$) for use as a CO detector. This electrode system was biased at a constant 0.71 V from an external source. The electrochemical sensor had a sensitivity of 500 ppm of CO and the authors concluded that a reasonable goal is to reduce the detection limit to 100 ppm. However, since the Environmental Protection Agency (EPA) has established 50 ppm as a tolerance level, the inability of the La Conti cell to detect below 100 ppm would exclude that device from further practical consideration.

La Conti and Maget erroneously focus their approach on the operation of the electrode as an oxygen electrode; thus, they first establish the potential at which the oxygen reaction current is zero and then they test the sensitivity of the electrode towards CO oxidation at such pre-established potential, dictated by the electrochemistry of oxygen on platinum; consequently, they found a lower limit of sensitivity of about 500 ppm CO in air.

According to the present invention, a limit of detection approximately 2 ppm can be achieved by selecting and appropriately biasing a gas diffusion electrode according to the principles described below. This is comparable to commercially available three electrode systems such as shown in Oswin et al U.S. Pat. No. 3,776,832.

Carbon monoxide (CO) can be oxidized electrochemically at an anode according to the reaction:

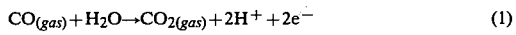
$$CO_{(gas)} + H_2O \rightarrow CO_{2(gas)} + 2H^+ + 2e^- \quad (1)$$

This reaction occurs in an electrochemical cell, coupled to an electrochemical reduction taking place at the cathode:

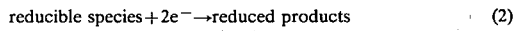
$$\text{reducible species} + 2e^- \rightarrow \text{reduced products} \quad (2)$$

The nature of the cathodic materials involved in (2) will be discussed below.

It is known that the rate of the overall cell reaction (reactions 1 and 2 coupled) is measured by the current (I) circulating in the external circuit which connects the anode to the cathode. The value of the current is dependent upon several parameters, of which the most relevant are: (i) the potential of the anode ($V_a$), (ii) the potential of the cathode ($V_c$), (iii) the concentration (or partial pressure) of the CO ($P_{co}$), (iv) the concentration of the reducible species ($C_r$), (v) the temperature (T), and (vi) the concentration of other species in solution.

The conditions that allow the electrochemical cell to function as a detector of CO are such that the effect of factors (i), (ii), (iv), (v), and (vi) is rendered negligible, thereby leading to a one-to-one relationship between current (I) and CO concentration ($P_{co}$).

The effect of anode potential ($V_a$) on the rate of CO oxidation (or current, I) can be understood with reference to FIG. 1 of the drawings.

In region (a) no reaction takes place (or the rate of the reaction is exceedingly small); in region (b) the rate increases as the anode potential is increased, i.e., the reaction is activated by the electrode polarization and increasing amounts of the available CO are consumed; in region (c) all the available CO is consumed, and an increase in $V_a$ within this region does not lead to an increase in I (limiting current conditions); in region (d) a new reaction takes place in addition to CO oxidation, namely, water discharge:

$$H_2O \rightarrow \tfrac{1}{2}O_2(gas) + 2H^+ + 2e^- \quad (3)$$

Region (e) is observed if a reducible species is present in the gas mixture; thus, in air a reduction takes place at the electrode, namely, oxygen reduction:

$$\tfrac{1}{2}O_2 + 2H^+ + 2e^- \rightarrow H_2O \quad (4)$$

Clearly, the only region appropriate for the quantitative detection of CO is region (c), where no parallel reactions (water discharge or oxygen reduction) interfere and in which the current is independent of the potential for CO oxidation. The value of $V_a$ in region (c) is from about 1.1 volts to about 1.3 volts versus a reversible hydrogen electrode in the same solution, but the exact values depend on the detailed structure of the anode.

The cell is biased by means of a constant potential $\Delta V$ applied between the cathode and anode; thus, the anode potential, $V_a$, is given by $$V_a = V_c + \Delta V \quad (5)$$

For a non-polarizable electrode, the slope of the I vs. V relation in region (a) is such that for all values of I of interest, there is no appreciable departure of $V_c$ from the value corresponding to zero current, namely, the reversible potential, $E_c$, of the electrode.

On the other hand, consideration must be given to the fact that the value of $E_c$ is dependent upon the concentration of reducible and other species in solution (as governed by the well-known Nernst equation). Therefore, the value of $V_a$ cannot be kept strictly constant, $V_c$ being somewhat dependent on current and on concentration of one or several species in solution.*

*For a $PbO_2/PbSO_4$ electrode the value of $E_c$ is a function of the concentration (strictly, the activity) of sulfuric acid in the solution.

For these reasons, the biasing to the current limited portion (region (c)) to operate the sensing electrode is essential for the success of a detector: were the electrode to be used in region (b), the small variations in $V_c$ resulting from a slightly polarizable character of the cathode, or even local variations in concentration in the vicinity of the cathode during operation, would result in large variations in current and hence inaccurate detection.

In addition, the sensitivity of the sensing electrode is greatest in region (c), while in region (b) the sensitivity may decrease ten-fold or more for each 120 mV decrease in the value of $V_a$. Thus, the operation of the sensing electrode in region (c) is a basic element of the detector described herein.

Returning now to the La Conti et al reference, their electrode was not operated in the limiting current region; indeed, from FIG. 7 in that paper it can be seen that the current-voltage curve for CO oxidation was not determined at the potential at which their sensing electrode was operated, the choice of that potential being made on quite different theoretical principles and by a different experimental method; briefly, their method consisted in determining in the absence of CO, the potential, $V_{a,o}$ at which the current through the sensing electrode was exactly zero, thereafter operating the electrode in the presence of CO at that same potential. The rationale of that method is connected with the side reactions referred to in our FIG. 1 as causing regions (d) and (e) of the curve.

It is immediately apparent from FIG. 1 that it is unnecessary to choose $V_a$ exactly equal to $V_{a,o}$ to achieve a practical detection system. In fact, because of the nature of the side reactions involved (oxygen reduction in region (e) and oxygen evolution in region (d)) there is a region of potentials (approximately from 0.9 volts to 1.4 volts vs. a reversible hydrogen electrode in the same solution) in which the rate of oxygen reduction or oxygen evolution is negligibly low. The residual current observed in the absence of CO between 0.9 and 1.4 volts is mainly due to the formation or reduction of an oxide layer on the electrode and the value of that current is much smaller than the CO oxidation current, provided the latter is in the limiting current range.

In short, the much higher sensitivity of the detector described herein compared to that of La Conti et al, is due to the basic difference in the principles of operation of the sensing electrode and operating potential. In this connection, while Teflon bonded noble metal catalyst electrodes on a Teflon membrane support are known in the art, the present invention adopts same in a unique way to achieve a high degree of sensitivity.

BRIEF DESCRIPTION OF THE DRAWINGS

The above and other objects and advantages and features of the invention will become more apparent when considered in conjunction with the accompanying drawings wherein:

FIG. 5a is a cross-sectional view of an electrochemical cell which incorporates the invention hereof, and FIG. 5b is a front end view.

Figure 1:
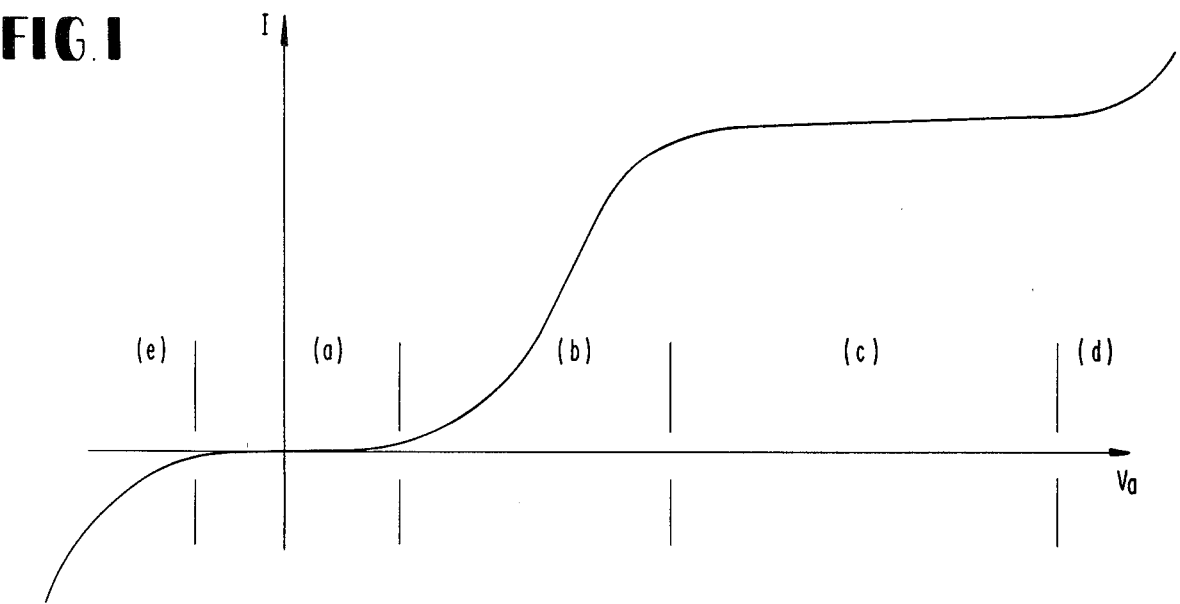
FIG. 1 is a curve which illustrates a general current versus voltage plot for an electrochemical reaction.

Referring now to the drawings, in FIG. 1, it can be seen that for the purposes of a useful detector, the electrode materials must be selected such that the cathode always operates within section (a) of the curve of FIG. 1 and that the slope of the current versus the cathode voltage $V_c$ must be large so as to permit the cathode to sustain or support fairly large currents without appreciable departure of the potential $V_c$ from its reversible value, $E_c$. The cathode therefore must be of a material which is (1) reducible and has enough capacity to provide a reasonably long life for the cell, (2) it must be reversible within the range of currents produced by the cell, (3) it must be stable (free of corrosion) in the electrolyte system chosen, (4) if a soluble reducible species is used as part of the counter electrode system, such material must not be reduced at the potential of the anode and, finally, if the reduced product is soluble, it must not be oxidized at the potential of the anode. Accordingly, based upon these requirements for a carbon monoxide sensor, a lead dioxide cathode or counter electrode system is most highly preferred, both because of its satisfaction of all of the requirements mentioned above, and because of its capacity requirements for a reasonably long lived cell.

While a number of gas diffusion anodes may be used, a Teflon bonded noble metal catalyst such as platinum black particles bonded to a Teflon base is highly suitable in combination with the lead dioxide counter electrode in sulfuric acid electrolyte at a potential of 0.58 volts between them. "Teflon is a Dupont trademark for its polytetrafluoroethylene fluorocarbon.

Figure 2:
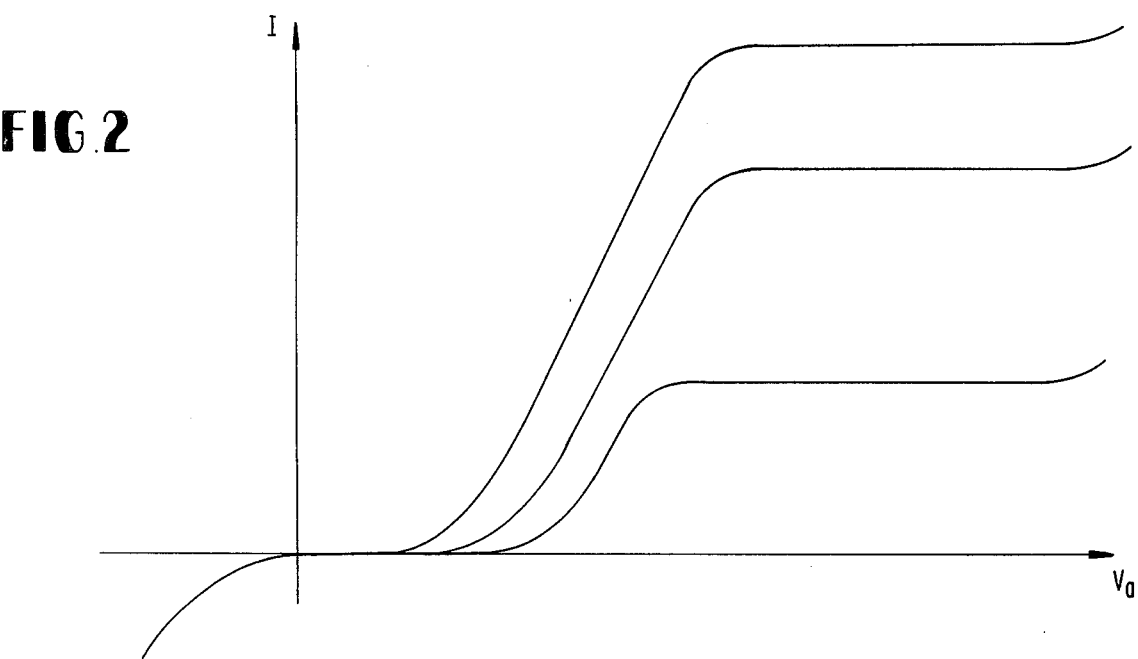
FIG. 2 is a plot of a family of such curves with different concentrations of reactant (e.g., CO)
Figure 3:
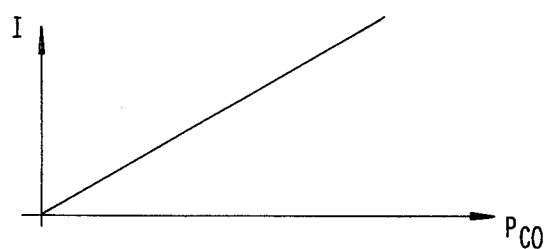
FIG. 3 illustrates the linearity of the relationship between current and partial pressure of carbon monoxide ($P_{co}$) in region (c) of the family of curves shown in FIG. 2.

The family of curves known in FIG. 2 illustrates the effect on current of variations in the carbon monoxide concentration in a cell structure as discussed generally above. In this family of curves, it will be noted that for curve P1, the partial pressure of carbon monoxide is less than that for curve P2 which, in its turn, is less than the partial pressure of carbon monoxide in curve P3. The linearity of the relationship between current and concentration (for plateau region c) is illustrated in the curve shown in FIG. 3 where the current is plotted against partial pressure ($P_{CO}$). The curves illustrated in FIGS. 1, 2 and 3 are typical curves and plotted with respect to a standard temperature and pressure. That is to say, inherent background current has been nulled or zeroed out of these curves. In addition, the curves of FIG. 2 are assumed to be at the same temperature. That is to say, it is standard practice to provide temperature compensation and background current elimination for such curves and the CO sensor disclosed herein requires the same.

DESCRIPTION OF GENERAL CELL STRUCTURE

Figure 4B:
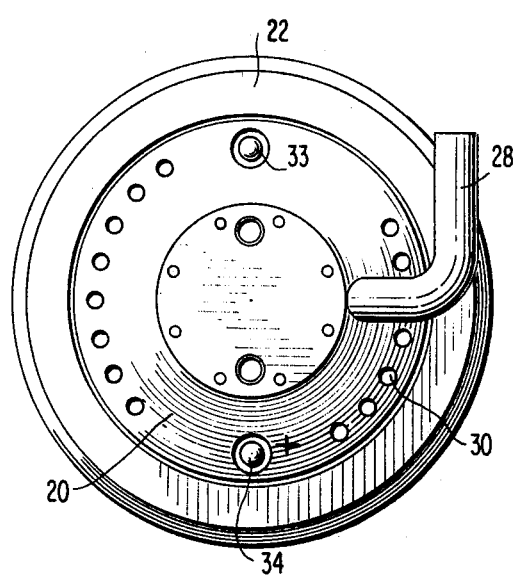
FIG. 4 is a functional block diagram of an electrochemical CO detector incorporating the invention.
Figure 4A:
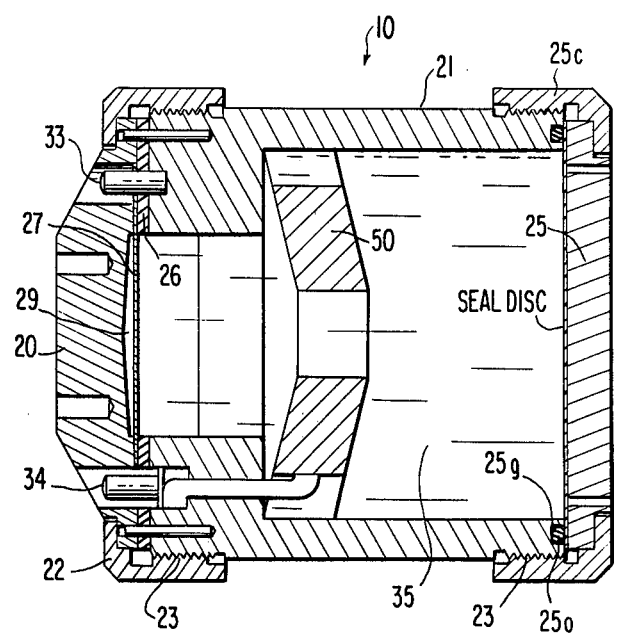
Figure 4:
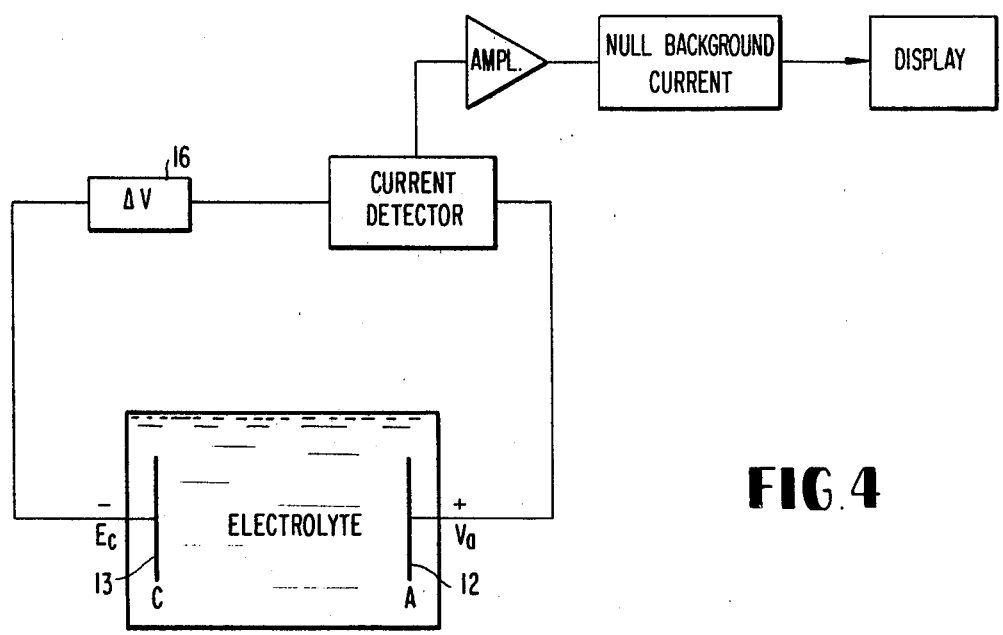

Referring now to the block diagram in FIG. 4, the polarographic electrochemical CO carbon monoxide detector of the present invention is shown as including a cell 10 containing an electrolyte 11, a sensing electrode or anode 12, and a counter electrode or cathode 13. The cell also includes a means (not shown in FIG. 4) for introducing the carbon monoxide gas to the catalytic or polarized anode 12. Leads 14 and 15 connect the cell electrodes 12 and 13, respectively, to the external circuit.

As indicated above, the anode 12 is a polarized anode which is exposed to the carbon monoxide-containing atmosphere and, typically, utilizes a noble metal catalyst, most preferably platinum. The electrolyte 11 is, most preferably, sulfuric acid and the counter electrode or cathode 13 is most preferably lead dioxide on lead. The cathode, being non-polarizable, is at an approximately constant potential, designated as $E_c$ on FIG. 4. The power supply 16 maintains a constant potential difference $\Delta V$ between the cathode 13 and the anode 12 thereby imposing on the anode an approximately constant potential $V_a$ which is equal to the sum of the cathode potential $E_c$ plus the potential difference $\Delta V$. The power supply also incorporates conventional means, not shown, to adjust the voltage $\Delta V$ to any desired value, and, as discussed above, the value is set to assure that the voltage at the sensing electrode 12 is within the plateau region of the curve of FIG. 1, in order (1) to significantly increase the sensitivity of the detector, and (2) to prevent minor variations in $V_c$ from affecting the current output of the sensor for a given CO concentration. The power supply may also include an amplification system and meter to measure and display the current flowing through the cell. In FIG. 4, a zero impedance current detector is shown separate from the voltage source 16 for purposes of explaining this invention, but in usual practice, it is a part of the voltage source 16. The amplifier includes (1) means to adjust the display to zero when no carbon monoxide is present in the sample gas and hence compensates for inherent background current of the electrochemical device, a technique well-known in the art, (2) means to compensate for temperature dependence of the cell output, typically thermistors are used for this purpose, a technique also well-known in the art, and (3) means to transform the input current-concentration curve into the desired output display-concentration curve on the display. This transformation means can merely be the scale of the display or, if desired, electrical circuitry may be utilized to digitize the input current concentration curve into a digital display if desired, and (4) means to match the output reading to the calibration gas value.

Such circuitry for the temperature compensation and amplification of the current as well as the transformation of the current to a suitable scale, are all well-known expedients in the art and form no part at all of the present invention. The present invention is concerned basically, and most particularly with respect to the combination of the anode-cathode materials and electrolytes, and the appropriate selection of the potential range for sensing carbon monoxide concentrations in a conventional electrochemical polarographic technique. The improvement, then, is basically in the materials and methods and most particularly in the combination of the lead dioxide counter electrode and the gas diffusion anode utilizing a noble metal catalyst, preferably platinum, biased to the plateau or region (c) of the curve in FIG. 1.

DETAIL DESCRIPTION OF CELL STRUCTURE INCORPORATING THE INVENTION

A typical cell incorporating the invention is shown in cross-section in FIG. 5a and FIG. 5b. The cell 10 includes injection molded plastic body housing members and is constituted by a gas chamber head 20, a cathode-electrolyte chamber body 21 and threaded closure member 22, these parts being fastened together by closure member threads 23 and gas chamber head screws (not shown). The electrolyte chamber body 21 and cathode chamber head 25 are secured in sealing relation by threaded closure member 25c but may be formed integral with one another instead of as the separate units illustrated. An O-seal ring 25o in annular groove 25g and a flexible seal disc seals the unit. Conventionally, the anode head has a blind bore (not shown) for receiving a temperature compensating thermistor (not shown). Other configurations for the body members are obviously possible.

A gas diffusion anode 27 which is a Teflon-bonded noble metal catalyst on a Teflon membrane support is secured between a spacer member-gasket 26 and the gas chamber head 20 and seals or prevents the leakage of any electrolyte from the chamber between spacer 26 and gas chamber head 20. Gas inlet passage 28 is formed in gas chamber head 20 and leads to a gas chamber or space 29 on the Teflon side of the gas diffusion anode 27. A plurality of gas outlet passages 30 are provided in gas chamber head 20 so that a well distributed flowing stream of gas may be provided in the chamber 29.

It will be noted that an electrical lead 33 is connected to the noble metal catalyst anode and constitutes the anode lead 14 of FIG. 4. This anode lead may be any other form of electrical lead through or sealed lead-in to be electrically connected to the anode. A similar lead 34 is connected to the cathode 50 (cathode lead 15 of FIG. 4).

The electrolyte chamber body 21 forms a chamber or space 35 into which is introduced the electrolyte by means of a filling vent cap (not shown). Preferably the electrolyte chamber 35 is filled with sulfuric acid (66%).

The lead dioxide electrode 50 is a porous paste body member so that a relatively large surface area of lead dioxide is exposed to the electrolyte. Moreover, the lead dioxide electrode 50 is chosen for the purposes set forth earlier herein so that the cathode always operates within section (a) of the curve of FIG. 1 and the slope of the current versus $V_c$ curve is very large. This permits the cathode to sustain the largest currents expected without any appreciable departure of the potential $V_c$ from its reversible value, $E_c$, and hence such an electrode is called a reversible or non-polarizable electrode in the art.

The material of which the sensing electrode or anode is made must meet the following requirements:

(1) Section (b) of the curve shown in FIG. 1 must not extend too far in the anode direction as it would obliterate the useful measuring section (c). This means that the anode must exhibit good catalytic properties towards the oxidation of carbon monoxide.

(2) It must show good mass transfer characteristics between the sample gas and the electrode-electrolyte interface where the electrochemical oxidation takes place.

(3) It must be stable in the electrolyte and at the potential ($V_a$) chosen for its operation.

A gas diffusion electrode utilizing Teflon-bonded noble metal catalyst, such as platinum, is highly preferred.

The reversible potential of the $PbO_2/PbSO_4$ electrode in 10 M $H_2SO_4$ is approximately 1.7 volts versus a reversible hydrogen electrode. The anode is polarized to a value selected to be in the range between $-0.4$ volts and $-0.6$ volts with respect to the cathode. Typical currents obtained fall within 0 and 1 milliamp; at these currents the $PbO_2/PbSO_4$ electrode shows no appreciable polarization. Hence, the anode potential is maintained at a selected value in the range of 1.1 volts to 1.3 volts versus the reversible hydrogen electrode, regardless of the CO concentration in the sample gas (i.e., regardless of current flowing through the cell). The most advantageous voltage used to date was 1.12 volts. Furthermore, oxygen evolution does not occur below 1.3 volts (vs. RHE) and oxygen reduction does not occur above 1.1 volts (vs. RHE). In addition, the determination of CO oxidation currents vs. potential on the electrodes used as sensing electrodes, shows a fairly constant value in the range 1.1 to 1.3 volts, thus conforming to the principles outlined above.

While I have described my invention in relation to a carbon monoxide sensor using anodic detection, it is obvious that the principles of the invention can be applied to cathodic gas detectors.

What I claim is:

1. In a method of operating an electrochemical gas measuring system consisting of a gas diffusion sensing electrode, an electrolyte, a non-polarizable, non-catalytic counter electrode, means for applying a bias potential between said electrodes, and means indicating the current flowing as a function of the gas concentration, the improvement comprising increasing the sensitivity of the system to a selected gas species at said gas diffusion sensing electrode by biasing said sensing electrode to a point in the limiting current plateau region of the current voltage curve for the electrochemical reaction of the gas at the sensing electrode, independent of the potential for oxidation of said selected gas species for the sensing electrode.

2. An electrochemical system as defined in claim 1 wherein:
(1) said gas diffusion sensing electrode is a polytetrafluoroethylene-bonded noble metal catalyst on a polytetrafluoroethylene membrane support,
(2) said counter electrode is $PbO_2/PbSO_4$,
(3) said electrolyte is sulfuric acid.

3. The invention defined in claim 2 wherein said noble metal catalyst is platinum black.

4. The invention defined in claim 3 wherein said system measures CO concentration to at least 2 parts per million.

* * * * *